(12) United States Patent
Satonaka et al.

(10) Patent No.: US 8,420,061 B2
(45) Date of Patent: Apr. 16, 2013

(54) ULTRAVIOLET ABSORBER WATER-DISPERSED COMPOSITION

(75) Inventors: Kenya Satonaka, Osaka (JP); Toshiyuki Itoh, Tokyo (JP); Yusuke Tanaka, Tokyo (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/971,064

(22) Filed: Dec. 17, 2010

(65) Prior Publication Data

US 2011/0117034 A1 May 19, 2011

Related U.S. Application Data

(63) Continuation of application No. 12/740,118, filed as application No. PCT/EP2008/054703 on Nov. 10, 2008, now abandoned.

(30) Foreign Application Priority Data

Nov. 12, 2007 (JP) ................................. 2007-293190

(51) Int. Cl.
*A61K 8/00* (2006.01)
*A61K 8/18* (2006.01)
*A61Q 17/04* (2006.01)

(52) U.S. Cl.
USPC .......................................................... 424/59

(58) Field of Classification Search ...................... 424/59
See application file for complete search history.

(56) References Cited

U.S. PATENT DOCUMENTS

| | | | | |
|---|---|---|---|---|
| 5,637,293 A * | 6/1997 | Honda | ............................ | 424/62 |
| 5,980,872 A | 11/1999 | Luther et al. | | |
| 6,818,206 B2 | 11/2004 | Candau et al. | | |
| 2005/0002994 A1 | 1/2005 | Goppel | | |
| 2006/0275226 A1* | 12/2006 | Dahms et al. | .................... | 424/59 |
| 2009/0136437 A1* | 5/2009 | Springer et al. | ................ | 424/59 |
| 2010/0080833 A1* | 4/2010 | Rossow et al. | ................ | 424/401 |

FOREIGN PATENT DOCUMENTS

| | | |
|---|---|---|
| EP | 1284131 A | 2/2003 |
| EP | 1285648 A | 2/2003 |
| GB | 2433499 A | 6/2007 |
| JP | 2000-501064 | 2/2000 |
| JP | 2003-137719 | 5/2003 |

OTHER PUBLICATIONS

English Language Abstract of EP 1284131 Printed on Jul. 29, 2010.
English Language Abstract of 1285548 Printed on Jul. 29, 2010.

* cited by examiner

*Primary Examiner* — Mina Haghighatian
*Assistant Examiner* — Luke Karpinski
(74) *Attorney, Agent, or Firm* — Shiela A. Loggins

(57) ABSTRACT

Disclosed is an ultraviolet absorber water-dispersed composition, comprising the following components (A) and (B);
(A) a benzotriazole-type ultraviolet absorber represented by general formula (1) below

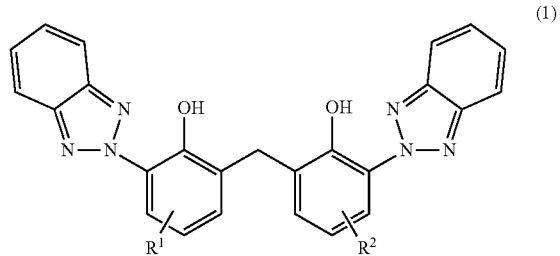

(1)

wherein $R^1$ and $R^2$ denote alkyl groups having a carbon number from 1 to 18, may be identical or different, and may be substituted by one or two or more groups selected from the group consisting of alkyl groups having a carbon number from 1 to 4, and cycloalkyl groups and aryl groups both having a carbon number from 5 to 12; and
(B) polyglycerol monoalkyl ester with a mean degree of polymerization of glycerol of 5 or more.
The water-dispersed composition is capable of stably maintaining the dispersed state of benzotriazole-type ultraviolet absorbers even in the presence of salt.

9 Claims, No Drawings

ULTRAVIOLET ABSORBER WATER-DISPERSED COMPOSITION

This application is a continuation of application Ser. No. 12/740,118, filed on Apr. 28, 2010 now abandoned which is the National Stage of International Application PCT/EP2008/054703, filed Nov. 10, 2008, the contents of which are herein incorporated by reference.

The present invention relates to an ultraviolet absorber water-dispersed composition, and more specifically relates to an ultraviolet absorber water-dispersed composition having excellent salt tolerance, and even in the presence of salt, being capable of inhibiting the agglomeration of a benzotriazole-type ultraviolet absorber and stably maintaining the dispersed state.

Ultraviolet light may be roughly classified into the UV-C region from 200 nm to 280 nm cut by the ozone layer, the UV-B region from 280 nm to 320 nm causing so-called sunburn, that is to turn the skin red due to exposure, and the UV-A region from 320 nm to 400 nm causing darkening after the redness is reduced. Not only such harm to the skin of the UV-A and -B mentioned above, recent studies suggested that UV-A had some effect on pigmentation, dry skin, rough skin, and skin sagging, and the harm of ultraviolet has been widely recognized. Moreover, environmental factors, such as the depletion of the ozone layer, is also considered, and thus there is a higher demand on cosmetics for ultraviolet protective functions.

However, among ultraviolet protective agents to be blended in cosmetics, organic ultraviolet absorbers generally have problems, such as (1) being inferior in solubility in oils generally used for cosmetic products, particularly in silicones, (2) being sticky and causing an unfavorable feel in use, (3) being inferior in light stability, and (4) causing change in color and smell over time. In contrast, since particulate titanium oxide and particulate zinc oxide, which are inorganic ultraviolet scattering agents, have problems such as (1) deteriorating the usability, (2) whitening upon application, and (3) having photocatalytic activity, they were limited in the amount to be blended into cosmetics. In addition, the actual condition was that almost no ultraviolet protective agent existed in which a single ultraviolet protective agent alone protects widely over the UV-A and -B regions.

With such being the situation, reported was a method for manufacturing a benzotriazole-type ultraviolet absorber that is excellent in light stability, has a wide range of ultraviolet absorption spectrum, and is insoluble in water and oils generally used for cosmetics (Patent Document 1). Furthermore, a technique is disclosed in which this substance is particulated to a mean particle diameter for demonstrating favorable ultraviolet protection capability in water phase components in the presence of alkyl polyglucoside or its ester to improve the convenience in formulation design (Patent Document 2), and products according to this technique are already on the market (TINOSORB® M: Ciba (Ciba Holding Incorporated)).

However, cosmetics are generally blended with salt, typically as amino acids, chelators, and buffers, and particularly water-in-oil emulsion cosmetics are often blended with salt such as magnesium sulfate and sodium chloride in the formulation to improve emulsion stability, which results in disadvantages of this technique in which combination of salt causes agglomeration of the benzotriazole-type ultraviolet absorber and thus the ultraviolet protection effect is reduced.

In addition, a dispersion is also disclosed that uses an amphipathic copolymer consisting of a hydrophilic block and a hydrophobic block (Patent Document 3). Since the amphipathic copolymer is not a dispersant excellent in salt tolerance, such disadvantage was still considered that combination of salt caused agglomeration of the benzotriazole-type ultraviolet absorber and thus the ultraviolet protection effect was reduced.

Patent Document 1: Japanese Laid-open Patent [Kokai] Publication No. Hei 04-290877
Patent Document 2: Japanese Laid-open Patent [Kohyo] Publication No. 2000-501064
Patent Document 3: Japanese Laid-open Patent [Kokai] Publication No. 2003-137719

Therefore, there has been a demand for developing a technique in which, even when salt is blended, a benzotriazole-type ultraviolet absorber having high light stability and a wide range of ultraviolet absorption spectrum can be stably dispersed in a particulated state without developing agglomeration, and thus the ultraviolet protection effect can be effectively exhibited.

As a result of keen examination to solve the problems, the applicants found that, even in the presence of salt, a benzotriazole-type ultraviolet absorber can be stably exist in a particulated state without agglomeration by dispersing the benzotriazole-type ultraviolet absorber in water using polyglycerol monoalkyl ester with a mean degree of polymerization of 5 or more, and have come to complete the present invention.

That is, the present invention is an ultraviolet absorber water-dispersed composition, comprising the following components (A) and (B);
(A) a benzotriazole-type ultraviolet absorber represented by a general formula (1) below

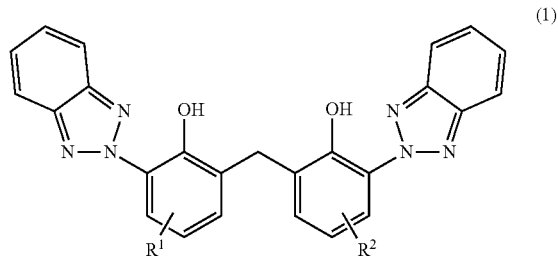

wherein
$R^1$ and $R^2$ denote alkyl groups having a carbon number from 1 to 18, may be identical or different, and may be substituted by one or two or more groups selected from the group consisting of alkyl groups having a carbon number from 1 to 4, and cycloalkyl groups and aryl groups both having a carbon number from 5 to 12]; and
(B) polyglycerol monoalkyl ester with a mean degree of polymerization of glycerol of 5 or more.

Since the water-dispersed composition of the present invention enables a benzotriazole-type ultraviolet absorber to be stably dispersed in a particulated state without agglomeration even in the presence of salt, it has a high degree of freedom in formulation design, can be blended with cosmetics of various formulations, and thus enables to give an excellent ultraviolet protection effect. Further, it can prevent color degradation due to the light of dyes contained in cosmetics and maintain the color tone.

Component (A) employed for the present invention is a benzotriazole-type ultraviolet absorber represented by the formula (1) below.

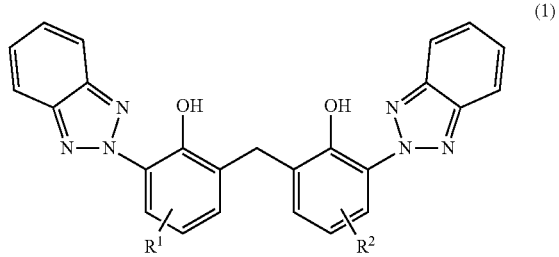

(1)

In the formula, $R^1$ and $R^2$ denote alkyl groups having a carbon number from 1 to 18, may be identical or different, and may be substituted by one or two or more groups selected from the group consisting of alkyl groups having a carbon number from 1 to 4, and cycloalkyl groups and aryl groups both having a carbon number from 5 to 12.

The benzotriazole-type ultraviolet absorber is a known methylenebis (hydroxyphenyl-benzo-triazole) derivative, and may be manufactured by a manufacturing process of, for example, Specification of U.S. Pat. No. 5,237,071, Specification of U.S. Pat. No. 5,166,355, Japanese Laid-open Patent [Kokai] Publication No. H04-290877, etc.

$R^1$ and $R^2$ in the Formula (1) are linear or branched alkyl groups having a carbon atom number from 1 to 18, and the examples may include methyl groups, ethyl groups, n-propyl groups, isopropyl groups, n-butyl groups, tert-butyl groups, tert-octyl groups, n-amyl groups, n-hexyl groups, n-heptyl groups, n-octyl groups, iso-octyl groups, n-nonyl groups, n-decyl groups, n-undecyl groups, n-dodecyl groups, tetramethylbutyl groups, tetradecyl groups, hexyldecyl groups, and octadecyl groups. In addition, these alkyl groups having a carbon atom number from 1 to 18 may be substituted by one or two or more substituents selected from the group consisting of alkyl groups having a carbon number from 1 to 4, and cycloalkyl groups and aryl groups both having a carbon number from 5 to 12. The cycloalkyl groups having a carbon atom number from 5 to 12 may include, for example, cyclopentyl groups, cyclohexyl groups, and cyclooctyl groups, and examples of the aryl groups both having the same may include phenyl groups and benzil groups.

Among these, it is favorable that $R^1$ and $R^2$ are identical and each of these groups is a methyl group, a 1,1,3,3-tetramethylbutyl group, or a tert-butyl group, and it is extremely favorable that each of $R^1$ and $R^2$ is a 1,1,3,3-tetramethylbutyl group. The extremely favorable 2,2'-methylenebis[6-(2H-benzotriazol-2-yl)-4-(1,1,3,3-tetramethylbutyl)phenol] can be manufactured according to the methods described in, for example, EXAMPLE 1 of Specification of U.S. Pat. No. 5,237,071 and Examples 1 through 3 of Japanese Laid-open Patent [Kokai] Publication No. H04-290877.

In addition, component (B) employed for the present invention is polyglycerol monoalkyl ester with a mean degree of polymerization of glycerol of 5 or more. Specifically, examples may include decaglyceryl caprate, decaglyceryl laurate, decaglyceryl myristate, decaglyceryl oleate, decaglyceryl stearate, decaglyceryl isostearate, hexaglyceryl caprate, hexaglyceryl laurate, hexaglyceryl myristate, hexaglyceryl oleate, hexaglyceryl stearate, hexaglyceryl isostearate, pentaglyceryl caprate, pentaglyceryl laurate, pentaglyceryl myristate, pentaglyceryl oleate, pentaglyceryl stearate, and pentaglyceryl isostearate.

Commercial products of decaglyceryl caprate may include Sunsoft Q-10Y and Q-10S (manufactured by Taiyo Kagaku Co., Ltd.), and commercial products of decaglyceryl laurate may include Sun Soft Q-12Y, Q-12S, and M-12J (manufactured by Taiyo Kagaku Co., Ltd.), NIKKOL Decaglyn 1-L (manufactured by Nikko Chemicals Co., Ltd.), and RYOTO-Polyglycerylester L-10D and L-7D (manufactured by Mitsubishi-Kagaku Foods Corp.). In addition, commercial products of decaglyceryl myristate may include Sun Soft Q-14Y and Q-14S (manufactured by Taiyo Kagaku Co., Ltd.), NIKKOL Decaglyn 1-M (manufactured by Nikko Chemicals Co., Ltd.), and RYOTO polyglyester M-10D, M-7D (manufactured by Mitsubishi-Kagaku Foods Corp.).

Commercial products of decaglyceryl stearate may include Sun Soft Q-18Y and Q-18S (manufactured by Taiyo Kagaku Co., Ltd.), NIKKOL Decaglyn 1-SV (manufactured by Nikko Chemicals Co., Ltd.), and RYOTO polyglyester S-15D (manufactured by Mitsubishi-Kagaku Foods Corp.), and commercial products of hexaglyceryl caprate may include Sun Soft Q-81F (manufactured by Taiyo Kagaku Co., Ltd.). In addition, commercial products of hexaglyceryl laurate may include NIKKOL Hexaglyn 1-L (manufactured by Nikko Chemicals Co., Ltd.), Glysurf 6mL (manufactured by Aoki Oil Industrial Co., Ltd.), and Unigly GL-106 (manufactured by Nippon Oil & Fats Co., Ltd.).

Commercial products of hexaglyceryl myristate may include NIKKOL Hexaglyn 1-M (manufactured by Nikko Chemicals Co., Ltd.), commercial products of hexaglyceryl laurate may include NIKKOL Hexaglyn 1-OV (manufactured by Nikko Chemicals Co., Ltd.), commercial products of hexaglyceryl stearate may include NIKKOL Hexaglyn 1-SV (manufactured by Nikko Chemicals Co., Ltd.) and EMAL-EXMSG-6K (manufactured by Nihon-Emulsion Co., Ltd.), and commercial products of hexaglyceryl isostearate may include Matsunate MI-610 (manufactured by Matsumoto Fine Chemical Co. Ltd.). In addition, pentaglyceryl caprate may include Sun Soft A-10E, pentaglyceryl laurate may include Sun Soft A12E and A-121 E, pentaglyceryl myristate may include Sun Soft A14E and A-141E, pentaglyceryl oleate may include Sun Soft A-17E and A-171E, pentaglyceryl stearate may include Sun Soft A-18E and A-181 E, and pentaglyceryl isostearate may include Sun Soft A-19E (all manufactured by Taiyo Kagaku Co., Ltd.).

Among these, those having an HLB of 14.5 or more are preferable, and those having an HLB of 15 or more are further preferable. Those having an HLB of less than 14.5 may take a longer time for dispersion of benzotriazole-type ultraviolet absorber in water phase components. Examples of polyglycerol monoalkyl ester with a mean degree of polymerization of 5 or more and having an HLB of 14.5 or more may include decaglyceryl caprate, decaglyceryl laurate, decaglyceryl myristate, decaglyceryl oleate, decaglyceryl stearate, decaglyceryl isostearate, hexaglyceryl laurate, pentaglyceryl laurate, pentaglyceryl myristate, pentaglyceryl stearate, and pentaglyceryl oleate, and those having an HLB of 15 or more may include decaglyceryl caprate and decaglyceryl laurate.

The amount of component (A) to be blended in the ultraviolet absorber water-dispersed composition is preferably from 10-50 mass % (hereinafter, simply referred to as "%"), and more preferably from 30-50%. In the case of less than 10%, there may be the cases in which the composition cannot be blended in a sufficient amount for exhibiting an ultraviolet prevention effect when blended with a cosmetic as a masterbatch (an intermediate material), and in the case of more than 50%, since it requires a large among of polyglycerol monoalkyl ester of component (B) for particulation, a cosmetic film easily may run with sweat, sebum, and the like when blended with a cosmetic.

In addition, the mass ratio of the content of component (B) to the content of component (A) is preferably from 0.05 to 0.5

(component (B)/component (A)), and more preferably from 0.1 to 0.3. In the case of less than 0.05, the ultraviolet absorber may not be dispersed to an optimum particle diameter, and in the case of more than 0.5, a cosmetic film may easily run with sweat, sebum, and the like when blended with a cosmetic.

In the ultraviolet absorber water-dispersed composition of the present invention, the aforementioned component (A) exists being dispersed in water, which is a dispersion medium, by component (B) acting as a dispersant, and such water includes purified water, spa water, deep water, and plant-extracted water extracted from plants such as apple water and plum fruit water. In addition, such water may contain, to the extent that effects of the present invention are not impaired, aqueous components like: alcohols, such as ethanol and isopropanol; polyhydric alcohols, such as glycerol, diglycerol, 1,5-pentanediol, 1,3-propanediol, 1,3-butylene glycol, 1,2-pentanediol, 1,6-hexanediol, ethylene glycol, diethylene glycol, dipropylene glycol, and propylene glycol; sugars, such as glucose, trehalose, maltose; sugar alcohols, such as mannitol and sorbitol; and preservatives, such as methylparaben and phenoxyethanol.

The ultraviolet absorber water-dispersed composition of the present invention can be manufactured by mixing water and aforementioned components (A) and (B), and uniformly dispersing and grinding the mixture according to a common method, and applicable dispersion devices include, for example, a two-roller mill, a three-roller mill, a ball mill, a sand mill, a bucket mill, a homomixer, a vertical bead mill, a horizontal bead mill, a pin bead mill, a colloid mill, an attritor, a superhigh pressure homogenizer, and an ultrasonic disperser.

The mean particle diameter of component (A) after dispersion process is preferably from 10-2000 nm, more preferably from 20-1500 nm, and further preferably ranging from 50-1000 nm. In the case of less than 10 nm, absorption in the UV-A region may be reduced, and in the case of more than 2000 nm, the ultraviolet prevention effect may be reduced and agglomeration and precipitation may be developed over time. It should be noted that, in this specification, a mean particle diameter means a mean particle diameter measured by a particle size distribution analyzer (Coulter N4 PLUS; manufactured by Bechman Coulter Inc.).

Since the ultraviolet absorber water-dispersed composition thus obtained is excellent in salt tolerance and includes a benzotriazole-type ultraviolet absorber stably dispersed, it can be blended with various cosmetics to impart the ultraviolet protection effect. The amount of the ultraviolet absorber water-dispersed composition of the present invention to be blended with a cosmetic is preferably an amount that the content of component (A), which is a benzotriazole-type ultraviolet absorber, in the cosmetic falls within a range from 0.1-10% in terms of solid content for good usability as a cosmetic and an excellent ultraviolet protection effect.

Into the cosmetic of the present invention, components generally blended into cosmetics may appropriately be blended, as needed. Within a range where effects of the present invention are not impaired, it may be blended with, for example: solid/semisolid oils, such as vaselines, lanolins, ceresins, microcrystalline waxes, carnauba waxes, candelilla waxes, higher fatty acids, and higher alcohols; liquid oils, such as squalenes, liquid paraffins, ester oils, diglycerides, triglycerides, silicone oils, olive oils, avocado oils, and mink oils; fluorine oils, such as perfluoropolyethers, perfluorodecalins, and perfluorooctanes; water- and oil-soluble polymers; surfactants; polyhydric alcohols; sugars; metal soaps; lecithins; amino acids; collagens; inorganic and organic pigments; various surface treatment powders; coloring agents, such as tar dyes and natural dyes; ethanols; preservatives; antioxidants; thickeners; pH adjusters; fragrances; ultraviolet absorbers; humectants; blood circulation accelerators; infrigidants; disinfectants; skin activators; and water.

Among these, by using, in particular, octyl methoxycinnamate as an ultraviolet absorber together with component (A), a synergistic ultraviolet prevention effect can be obtained. The octyl methoxycinnamate is a clear liquid in light yellow, has a slight characteristic odor, and is a versatile UV-B absorber employed for cosmetic products, and available commercial products of such may include Parsol MCX (manufactured by DSM Nutritional Products, Inc.), Uvinul MC-80 (manufactured by BASF SE), and Nomcort TAB (manufactured by Nisshin OilliO Group Ltd.). Moreover, when coloring agents are contained in a cosmetic, it can prevent color degradation of the agents due to light and maintain good appearance.

In addition, the cosmetic of the present invention is not particularly limited in form, type of product, etc. and examples of the possible form include water-in-oil, oil-in-water, water-dispersed, and powdery and examples of the possible product type may include: cosmetics for skin care, such as foaming and cream cleansers, makeup removers, massage creams, masks, facial lotions, emulsions, creams, serums, makeup bases, and sunscreens; makeup cosmetics, such as foundations, face powders, eyeshadows, eyeliners, mascaras, eyebrow makeups, concealers, lipsticks, and lip balms; and hair cosmetics such as hair mists, shampoos, conditioners, treatments, hair tonics, hair creams, pomades, mustache/hair waxes, hair dressing liquids, hair styling lotions, hair sprays, and hair dyes. Among these, cosmetics like sunscreens, foundations, and makeup bases easily exhibit the effects of the present invention.

Hereinafter, the present invention is described in detail with Examples and the like. It should be noted that they are merely for illustration and the technical scope of the present invention is not limited to them.

PRODUCTION EXAMPLE 1

Producing a benzotriazole-type ultraviolet absorber (2,2'-methylenebis[6-(2H-benzotriazol-2-yl)-4-(1,1,3,3-tetramethylbutyl)phenol):

In a double-jacket flask of 0.75 L tested at 1.5 bar overpressure and provided with a cryocooler, having a gas inlet tube and a receiving flask, and a vacuum connection tube, having a cold trap to a vacuum pump, 323.2 g (1.0 mol) of 4-(1,1,3,3-tetramethyl)butyl-6-benzotriazol-2-ylphenol and 16.5 g (0.55 mol) of paraformaldehyde were charged.

After evacuating the flask at 20 mbar and sealing it, the mixture was melted at a jacket temperature of 120° C., and consequently the pressure was increased to approximately 270 mbar. After that, 24.8 g (0.55 mol) of dimethylamine gas was incorporated into a melted material capable of being easily stirred at temperatures from 100° C. to 105° C. over 30 minutes. The final pressure is increased to from 900 mbar to 1000 mbar. The reaction mixture is heated to 135° C. and stirred at the temperature for two to four hours at a pressure raised to 1800 mbar. After cooling to 90° C., water from reaction together with unreacted amine were removed by decompressing and heating to 130° C. The pressure was alleviated with nitrogen, followed by adding 2.2 g (0.04 mol) of sodium methylate as a catalyst to the reaction mass, reducing the pressure at 200 mbar, and then rapidly heating to 200° C.

Separation of dimethylamine was observed at approximately from 145° C. to 155° C. After stirring at 200° C. and approximately 200 mbar for two to four hours, the deamination reaction was terminated, and the reaction was completed. After dissolving the melted material in 200 g of a xylene mixture, impurities were removed by neutralizing the alkaline catalyst with 3.2 mL of formic acid (85%) and filtering the solution at 130° C., and the filtrate was washed with 75 g of a xylene mixture. Crystallization occurred by cooling to approximately 0° C.

After suction filtering the viscous suspension and washing it with 100 g of a xylene mixture, the product was dried in a vacuum drying oven at 120° C. to obtain [2,2'-methylenebis [6-(2H-benzotriazol-2-yl)-4-(1,1,3,3-tetramethylbutyl)phenol]. Yield: a product of 294 g in a form of yellow powder (89.3% of a theoretical value based on consumed benzotriazolyl phenol), melting point 197.6° C., transmittance at 450 nm (5% in cloroform): 96.4%, transmittance at 500 nm: 97.7%.

EXAMPLE 1

In a 200 mL capacity beaker, 52 g of purified water and 8 g of decaglyceryl laurate (HLB: 15.5) were added and mixed. The mixture was charged into a dispermixer (LR-1 type; manufactured by Mizuho Industrial Co., Ltd.), and while stirring, 40 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill (Paint Conditioner; manufactured by Red Devil Inc.) to obtain a water-dispersed composition of 2,2'-methylenebis[6-(2H-benzotriazol-2-yl)-4-(1,1,3,3-tetramethylbutyl)phenol].

EXAMPLE 2

In a 200 mL capacity beaker, 78 g of purified water and 2 g of decaglyceryl laurate (HLB: 15.5) were added and mixed. The mixture was charged into a dispermixer, and while stirring, 20 g of 2,2'-methylenebis[6-(2H-benzotriazol-2-yl)-4-(1,1,3,3-tetramethylbutyl)phenol] obtained in Production Example 1 [obtained in Production Example 1](sic) was added and stirred for 5 minutes in the dispermixer. Subsequently, 200 g of φ 1.0 mm zirconia beads were added, and the mixture was subjected to dispersing and grinding process for 120 minutes with a sand mill to obtain a water-dispersed composition.

EXAMPLE 3

In a 200 mL capacity beaker, 89.5 g of purified water and 0.5 g of decaglyceryl laurate (HLB: 15.5) were added and mixed. The mixture was charged into a dispermixer, and while stirring, 10 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

EXAMPLE 4

In a 200 mL capacity beaker, 45 g of purified water and 10 g of decaglyceryl caprate (HLB: 16.5) were added and mixed. The mixture was charged into a dispermixer. While stirring, 45 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

EXAMPLE 5

In a 200 mL capacity beaker, 62 g of purified water and 8 g of pentaglyceryl laurate (HLB: 14.5) were added and mixed. The mixture was charged into a dispermixer, and while stirring, 30 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

COMPARATIVE EXAMPLE 1

In a 200 mL capacity beaker, 52 g of purified water and 8 g of decyl glucoside were added and mixed. The mixture was charged into a dispermixer, and while stirring, 40 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

COMPARATIVE EXAMPLE 2

In a 200 mL capacity beaker, 52 g of purified water and 8 g of polysorbate 20 (HLB: 16.7) were added and mixed. The mixture was charged into a dispermixer, and while stirring, 40 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

COMPARATIVE EXAMPLE 3

In a 200 mL capacity beaker, 52 g of purified water and 8 g of polysorbate 80 (HLB: 15.0) were added and mixed. The mixture was charged into a dispermixer, and while stirring, 40 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

COMPARATIVE EXAMPLE 4

In a 200 mL capacity beaker, 52 g of purified water and 8 g of decaglyceryl diisostearate (HLB: 11.1) were added and mixed. The mixture was charged into a dispermixer, and while stirring, 40 g of 2,2'-methylenebis[6-(2H-benzotriazol-2-yl)-4-(1,1,3,3-tetramethylbutyl)phenol] obtained in Production Example 1 was added and stirred for 5 minutes. Subsequently, 200 g of φ 1.0 mm zirconia beads were added, and the mixture was subjected to dispersing and grinding process for 120 minutes with a sand mill to obtain a water-dispersed composition.

COMPARATIVE EXAMPLE 5

In a 200 mL capacity beaker, 52 g of purified water and 8 g of decaglyceryl dilaurate (HLB: 12.0) were added and mixed. The mixture was charged into a dispermixer, and while stirring, 40 g of 2,2'-methylenebis[6-(2H-benzotriazol-2-yl)-4-(1,1,3,3-tetramethylbutyl)phenol] obtained in Production Example 1 was added and stirred for 5 minutes in the dispermixer. Subsequently, 200 g of φ 1.0 mm zirconia beads were added, and the mixture was subjected to dispersing and grinding process for 120 minutes with a sand mill to obtain a water-dispersed composition.

TEST EXAMPLE 1

Measurement of Mean Particle Diameter

The water-dispersed compositions obtained in Examples 1 through 5 and Comparative Examples 1 through 5 were stored at 50° C. for one month and diluted with purified water so as to contain 2,2'-methylenebis[6-(2H-benzotriazol-2-yl)-4-(1, 1,3,3-tetramethylbutyl)phenol] at a concentration of 0.01%, and mean particle diameters (D50) were measured by a particle size distribution analyzer (Coulter N4 PLUS; manufactured by Bechman Coulter Inc.). The results are shown in Table 1.

TEST EXAMPLE 2

Stability Test

The water-dispersed compositions obtained in Examples 1 through 5 and Comparative Examples 1 through 5 were stored at 50° C. for one month and evaluated the behavior of 2,2'-methylenebis[6-(2H-benzotriazol-2-yl)-4-(1,1,3,3-tetramethylbutyl)phenol] according to the criteria below. The results are shown in Table 1.
<Precipitation Evaluation>
Double Circle No change
O: Slight separation in upper layer
Δ: Precipitation of ultraviolet absorber
X: Caking of ultraviolet absorber at a lower portion

TEST EXAMPLE 3

Salt Tolerance Test

The water-dispersed compositions obtained in Examples 1 through 5 and Comparative Examples 1 through 5 were diluted with purified water so as to contain 2,2'-methylenebis [6-(2H-benzotriazol-2-yl)-4-(1,1,3,3-tetramethylbutyl)phenol] at a concentration of 0.5% and added with 0.5% of sodium chloride, and left standing at 50° C. for seven days to evaluate the behavior of 2,2'-methylenebis[6-(2H-benzotriazol-2-yl)-4-(1,1,3,3-tetramethylbutyl)phenol] according to the precipitation criteria above.

TABLE 1

|  | Test Example 1 D50 (nm) | Test Example 2 Stability | Test Example 3 Salt Tolerance |
| --- | --- | --- | --- |
| Example 1 | 197 | ◎ | ◎ |
| Example 2 | 185 | ◎ | ◎ |
| Example 3 | 200 | ◎ | ◎ |
| Example 4 | 195 | O | O |
| Example 5 | 198 | ◎ | ◎ |
| Comparative Example 1 | 200 | ◎ | X |
| Comparative Example 2 | 351 | Δ | X |
| Comparative Example 3 | 800 | Δ | X |
| Comparative Example 4 | 3000 | X | O |
| Comparative Example 5 | 2500 | X | ◎ |

According to Test Example 1, the stability of 2,2'-methylenebis[6-(2H-benzotriazol-2-yl)-4-(1,1,3,3-tetramethylbutyl)phenol] in a particulated state was excellent in Examples 1 through 5 and Comparative Examples 1 through 3, whereas the particle diameter became extremely large in Comparative Examples 4 and 5 and it was found that polyglycerol dialkyl ester was not suitable as a dispersant for the ultraviolet absorber. In addition, according to Test Examples 2 and 3, Examples 1 through 5 demonstrated excellent stability and salt tolerance, whereas Comparative Examples 4 and 5 showed the results that the over-time stability was inferior as a water-dispersed composition and Comparative Examples 1 through 3 showed the results that the salt tolerance was inferior.

EXAMPLES 6 AND 7 AND COMPARATIVE EXAMPLES 6 THROUGH 9

W/O Sunscreen Cream

Using the water-dispersed composition prepared in Example 1 and Comparative Examples 1 and 2, W/O sunscreen creams of the composition shown in Table 2 below were prepared in the preparation below, and the samples were applied on Transpore Tape (manufactured by 3M Corporation) uniformly at 2 mL/cm², followed by air drying for 15 minutes to measure in-vitro SPF with an SPF analyzer (UV-1000S; manufactured by Labsphere, Inc.). The results are also shown in Table 2.
Preparation:
Component (9) is added to oil phase components (1) through (8) that were heated and dissolved and the mixture was uniformly dispersed with a mixer. Water phase components (10) through (15), heated and dissolved in another container, were added to the dispersion and emulsified, and then cooled to room temperature to obtain the desired sunscreen creams.

TABLE 2

| Blended Components | (%) | | | | | |
| --- | --- | --- | --- | --- | --- | --- |
|  | Example 6 | Example 7 | Comp. Ex. 6 | Comp. Ex. 7 | Comp. Ex. 8 | Comp. Ex. 9 |
| (1) Polyoxyethylene-methylpolysiloxane copolymer | 3 | 3 | 3 | 3 | 3 | 3 |
| (2) Decamethylcyclopentasiloxane | 20.8 | 15.8 | 20.8 | 15.8 | 20.8 | 15.8 |
| (3) Neopentyl glycol dicaprate | 5 | 5 | 5 | 5 | 5 | 5 |

TABLE 2-continued

| | Blended Components | Example 6 | Example 7 | Comp. Ex. 6 | Comp. Ex. 7 | Comp. Ex. 8 | Comp. Ex. 9 |
|---|---|---|---|---|---|---|---|
| (4) | Squalene | 5 | 5 | 5 | 5 | 5 | 5 |
| (5) | Dextrin palmitate | 1.5 | 1.5 | 1.5 | 1.5 | 1.5 | 1.5 |
| (6) | Octyl methoxycinnamate | | 5 | | 5 | | 5 |
| (7) | Preservative | q.s. | q.s. | q.s. | q.s. | q.s. | q.s. |
| (8) | Antioxidant | q.s. | q.s. | q.s. | q.s. | q.s. | q.s. |
| (9) | Particulate titanium oxide 37.5% dispersion** | 20 | 20 | 20 | 20 | 20 | 20 |
| (10) | Purified water | Balance | Balance | Balance | Balance | Balance | Balance |
| (11) | Water-dispersed composition of Example 1 | 7 | 7 | | | | |
| (12) | Water-dispersed composition of comparative Example 1 | | | | | 7 | 7 |
| (13) | 1.3-butylene glycol | 4 | 4 | 4 | 4 | 4 | 4 |
| (14) | Preservative | q.s. | q.s. | q.s. | q.s. | q.s. | q.s. |
| (15) | Sodium chloride | 1 | 1 | 1 | 1 | 1 | 1 |
| | In-vitro SPF measurement | 30.4 | 50.3 | 20.4 | 35.3 | 24.4 | 43.2 |

*Rheopearl KL (manufactured by Chiba Flour Milling Co., Ltd.)
**Cosmeserve WP-UF (V) (manufactured by Dainihon Kasei Co., Ltd.)

As apparent from Table 2, Example 6 of the present invention demonstrated a higher ultraviolet protection capability compared to Comparative Example 6, in which no water-dispersed composition was blended. In addition, it was confirmed that Example 7 further added with octyl methoxycinnamate has a higher synergistic effect compared to Comparative Example 7, in which no water-dispersed composition was blended. In contrast, Comparative Example 8 using the water-dispersed composition of Comparative Example 1 and Comparative Example 9 further added with octyl methoxycinnamate showed the results inferior to the products of the present invention although the ultraviolet protection capability was slightly improved. According to these findings, Examples 6 and 7 were W/O sunscreen creams excellent in ultraviolet protection capability.

EXAMPLE 8 AND COMPARATIVE EXAMPLE 10

Shampoo

Using the water-dispersed composition prepared in Example 1, shampoos of composition shown in Table 4 below were prepared according to the preparation below for color degradation test under exposure to sunlight. That is, the shampoos were placed outdoors, and color tone changes of the shampoos due to light over days were visually evaluated based on the evaluation criteria below. The results are also shown in Table 3.

Preparation:

Components (1) through (13) are heated, followed by stirring and dissolving. The solution was cooled to room temperature, and then (14) and (15) were added and stirred to obtain the desired shampoos.

Criteria for Visual Evaluation of Color Tone

Evaluation was carried out by comparing with samples kept in a dark place at 25° C., ◯: No Change Δ: Some Color Degradation x: Serious Color Degradation

TABLE 3

| | Blended Components | Example 8 | Comparative Example 10 |
|---|---|---|---|
| (1) | Sodium laureth sulfate | 18.50 | 18.50 |
| (2) | (C12-14) Pareth sulfosuccinate-2 sodium | 6.00 | 18.50 |
| (3) | Sodium lauryliminodiacetate | 7.00 | 7.00 |
| (4) | Lauramidopropyl betaine | 15.00 | 15.00 |
| (5) | Methyl gluceth-20 | 2.00 | 2.00 |
| (6) | PEG-120 Methyl glucose dioleate | 2.00 | 2.00 |
| (7) | 1,3-Butylene glycol | 2.00 | 2.00 |
| (8) | Polyoxyethylene coconut oil fatty acid glyceryl | 2.00 | 2.00 |
| (9) | Polyquaternium-7 1% dispersion | 15 | 15 |
| (10) | Polyquaternium-10 1% dispersion | 25 | 25 |
| (11) | Chelator | q.s. | q.s. |
| (12) | Preservative | q.s. | q.s. |
| (13) | Purified water | Balance | Balance |
| (14) | Blue No. 1 | 0.01 | 0.01 |
| (15) | Water-dispersed composition of Example 1 | 5.00 | — |
| Color Tone Evaluation | Immediately after preparation | ◯ | ◯ |
| | One month after preparation | ◯ | Δ |

As shown in Table 3, the shampoo of the present invention in Example 8 maintained the color at the time of preparation. There was, however, color degradation in the shampoo of Comparative Example 10, and the color at the time of preparation was not maintained. From the results, it was found that a shampoo was obtained that has high lightfastness to ultraviolet light and is prevented from color degradation over time by adding the water-dispersed composition of the present invention to a cosmetic.

EXAMPLE 9

W/O Emulsion-Type Foundation

A W/O emulsion-type foundation of the formula below was prepared in the preparation below.

| Composition | (%) |
|---|---|
| (1) Squalene | 4.0 |
| (2) Octyl methoxycinnamate | 4.0 |
| (3) Dimethylpolysiloxane (6 cs) | 2.0 |
| (4) Decamethylcyclopentasiloxane | 12.8 |
| (5) Polyoxyethylene-methylpolysiloxane copolymer (HLB = 4.5) | 4.0 |
| (6) Preservative | q.s. |
| (7) Antioxidant | q.s. |
| (8) Purified water | Balance |
| (9) 1,3-Butylene glycol | 5.0 |
| (10) Water-dispersed composition of Example 1 | 10.0 |
| (11) Titanium oxide | 5.0 |
| (12) Sericite | 5.0 |
| (13) Coloring agent | q.s. |

Preparation:

Powder components (11) through (13), stirred and mixed by a Henschel mixer in advance, are added to oil phase components (1) through (7), and uniformly dispersed by a mixer. Components (8) through (10), mixed in another container, were added to the dispersion, and after emulsification, and the mixture was cooled to room temperature to obtain a W/O emulsion-type foundation.

The W/O emulsion-type foundation thus obtained had an in-vitro SPF value of 30.5, and thus it was excellent in the effect of protecting the skin from ultraviolet damages, and when applied on the skin, it was not sticky, easily spread, and excellent in makeup endurance.

EXAMPLE 10

Emulsion

An emulsion of the composition below was prepared in the preparation below.

| Composition | (%) |
|---|---|
| (1) Squalene | 3.0 |
| (2) Dimethylpolysiloxane (100 cs) | 0.2 |
| (3) Neopentyl glycol dicaprate | 1.0 |
| (4) POE (60) hydrogenated castor oil | 1.0 |
| (5) Carboxyvinyl polymer | 0.2 |
| (6) Sodium hyaluronate 1% aqueous solution | 3.0 |
| (7) *Pyrus cydonia* seed Extract 2% aqueous solution | 5.0 |
| (8) Potassium hydroxide | 0.1 |
| (9) 1,3-butylene glycol | 6.0 |
| (10) Water-dispersed composition of Example 2 | 3.0 |
| (11) Purified water | Balance |
| (12) Preservative | q.s. |
| (13) Chelator | q.s. |

Preparation (1) through (4) are mixed and heated. (5) through (13) are mixed and heated in another container. The (1) through (4) were added to the (5) through (13) and emulsified, and cooled to room temperature to obtain an emulsion.

The emulsion thus obtained had an in-vitro SPF value of 3.2, and was excellent in the effect of protecting the skin from ultraviolet damages, and when applied on the skin, it was an emulsion that was not sticky, was easily spread, gave moist texture because of the slight thickness thereof, and was excellent in stability without developing discoloration and the like to ultraviolet.

EXAMPLE 11

O/W Sunscreen Cream

An O/W sunscreen cream of the composition below was prepared in the preparation below.

| Composition | (%) |
|---|---|
| (1) Alkyl-modified carboxyvinyl polymer | 0.4 |
| (2) 1,3-Butylene glycol | 4.0 |
| (3) glycerol | 2.0 |
| (4) Water-dispersed composition of Example 1 | 5.0 |
| (5) Preservative | q.s. |
| (6) Chelator | q.s. |
| (7) Sodium hyaluronate 1% aqueous solution | 5.0 |
| (8) Purified water | 83.1 |
| (9) Potassium hydroxide | 0.2 |
| (10) PEG-40 hydrogenated castor oil isostearate | 0.3 |
| (11) Neopentyl glycol dicaprate | 3.0 |
| (12) Octyl methoxycinnamate | 3.0 |

Preparation

(10) through (12) are mixed and heated. (1) through (9) are mixed and heated in another container. The (10) through (12) were added to the (1) through (9) and emulsified, and cooled to room temperature to obtain a cream.

The O/W sunscreen cream thus obtained had an in-vitro SPF value of 16, and was excellent in the effect of protecting the skin from ultraviolet damages, and when applied on the skin, it was an O/W sunscreen cream that was not sticky, was easily spread, and gave moist texture because of the slight thickness thereof.

EXAMPLE 12

Amino Acid Based Foaming Cleanser

A foaming cleanser of the composition below was prepared in the preparation below.

| Composition | (%) |
|---|---|
| (1) Sodium lauroyl glutamate | 35.0 |
| (2) Potassium laurate | 3.5 |
| (3) Cocamid methyl mEA | 1.0 |
| (4) Ceteareth-60 myristyl glycol | 1.0 |
| (5) 1,3-Butylene glycol | 20.0 |
| (6) Purified water | Balance |
| (7) PCA-Na 50% aqueous solution | 5.0 |
| (8) Water-dispersed composition of Example 3 | 5.0 |
| (9) Preservative | q.s. |
| (10) Blue No. 1 | q.s. |
| (11) Antioxidant | q.s. |

Preparation:

(1) through (11) are heated and mixed to be uniformly dissolved. The mixture was cooled to 30° C. by stirring to obtain an amino acid based foaming cleanser.

The foaming cleanser thus obtained was excellent in product stability without developing discoloration due to ultraviolet.

EXAMPLE 13

Eyeliner

An eyeliner of the composition below was prepared in the preparation below.

| Composition | (%) |
|---|---|
| (1) Sorbitan sesquioleate | 0.3 |
| (2) Polyoxyethylene sorbitan monooleate (20 E.O.) | 0.1 |
| (3) Polyoxyethylene-modified silicone (HLB = 4.5) | 0.5 |
| (4) Decamethylcyclopentasiloxane | 29.4 |
| (5) Light liquid isoparaffin | 17.5 |
| (6) Dextrin palmitate | 2.0 |
| (7) Organic modified bentonite | 1.0 |
| (8) Black Iron oxide | 14.0 |
| (9) Preservative | q.s. |
| (10) Purified water | Balance |
| (11) 1,3-Butylene glycol | 7.0 |
| (12) Water-dispersed composition of Example 5 | 5.0 |

Preparation:

(1) through (7) are heated and uniformly dissolved. After that, (8) is added and uniformly dispersed. (9) through (12) are heated and dissolved in another container. The (9) through (12) were added to the (1) through (8) and emulsified, and then cooled to room temperature to obtain an eyeliner.

The eyeliner thus obtained was an eyeliner excellent in stability without developing discoloration due to ultraviolet.

EXAMPLE 14

Mascara

A mascara of the composition below was prepared in the preparation below.

| Composition | (%) |
|---|---|
| (1) Purified water | 26.0 |
| (2) Polyvinyl pyrrolidone | 2.0 |
| (3) 1,3-Butylene glycol | 2.0 |
| (4) Cationized cellulose 1% aqueous solution | 10.0 |
| (5) Bentonite | 0.5 |
| (6) Triethanolamine | 1.7 |
| (7) Talc | 3.7 |
| (8) Yellow iron oxide | 0.9 |
| (9) Red iron oxide | 0.9 |
| (10) Black iron oxide | 4.8 |
| (11) Carnauba wax | 5.5 |
| (12) Beeswax | 9.0 |
| (13) Stearic acid | 2.0 |
| (14) Self-Emulsifiable glyceryl stearate | 2.0 |
| (15) Propylene glycol stearate | 2.0 |
| (16) Hydrogenated polyisobutene | 2.0 |
| (17) Decamethylcyclopentasiloxane | 4.0 |
| (18) Water-dispersed composition of Example 3 | 1.0 |
| (19) Preservative | q.s. |
| (20) Antioxidant | q.s. |
| (21) Alkyl acrylate copolymer emulsion | 20.0 |

Preparation:

Powder components (7) through (10), stirred and mixed by a Henschel mixer in advance, were added to water phase components (1) through (6) to be uniformly dispersed by a mixer. (11) through (20) were heated and dissolved in another container. The (11) through (20) were added to the (1) through (10) and emulsified, and then cooled to 40° C., followed by addition of (21) and cooled to room temperature to obtain a mascara.

The mascara thus obtained was excellent in the effect of protecting the eyelashes from ultraviolet damages, had a properly glossy appearance, and was excellent in adhesion to the eyelashes and product stability.

EXAMPLE 15

Treatment

A treatment of the composition below was prepared in the preparation below.

| Composition | (%) |
|---|---|
| (1) Cetanol | 3.0 |
| (2) Squalene | 1.0 |
| (3) Glyceryl 2-ethylhexanoate | 2.0 |
| (4) Cetyltrimethylammonium chloride | 5.5 |
| (5) Hydroxypropyl methyl cellulose | 0.2 |
| (6) Citric acid | 0.1 |
| (7) Water-dispersed composition of Example 3 | 1.0 |
| (8) Purified water | Balance |
| (9) Preservative | q.s. |
| (10) Chelator | q.s. |

Preparation (1) through (4) are mixed and heated. (5) through (10) are mixed and heated in another container. The (1) through (4) were added to the (5) through (10) and emulsified, and cooled to room temperature to obtain a treatment.

The treatment thus obtained was excellent in the effect of protecting the hair from ultraviolet damages and capable of maintaining a glossy appearance of the hair, inhibiting the drying out of damaged hair, and giving a moist and soft feel.

EXAMPLE 16

Hair Styling Cream

A hair styling cream of the composition below was prepared in the preparation below.

| Composition | (%) |
|---|---|
| (1) Isoparaffin | 7.9 |
| (2) Dimethylpolysiloxane (500 cs) | 7.0 |
| (3) Polyoxyethylene-methylpolysiloxane copolymer (HLB = 4.5) | 1.5 |
| (4) Isotridecyl isononanoate | 1.0 |
| (5) Acrylic resin alkanol amine liquid | 3.0 |
| (6) Isostearic acid | 0.1 |
| (7) Purified water | Balance |
| (8) Glycerol | 3.0 |
| (9) Water-dispersed composition of Example 4 | 5.0 |
| (10) Ethanol | 6.0 |
| (11) Magnesium sulfate | 1.0 |
| (12) Polyethylene glycol (molecular weight 10000) | 2.0 |
| (13) Preservative | q.s. |

Preparation (1) through (6) are heated and uniformly dispersed. (7) through (13) are heated and dissolved in another container. The (7) through (13) were added to the (1) through (6) and emulsified, followed by cooling to room temperature to obtain a hair styling cream.

The hair styling cream thus obtained was a hair styling cream excellent in the effect of protecting the hair from ultraviolet damages, and when applied on the hair, gave moist texture, was easily spread and not sticky, and excellent in styling maintenance.

EXAMPLE 17

Hair Mist

A hair mist of the composition below was prepared in the preparation below.

| Composition | (%) |
|---|---|
| (1) Purified water | Balance |
| (2) Glycosyl trehalose | 0.1 |
| (3) Glycerol | 1.5 |
| (4) 1,3-Butylene glycol | 1.0 |
| (5) Preservative | q.s. |
| (6) Hydrolyzed silk | 0.1 |
| (7) Hydrolyzed hyaluronic acid | 0.3 |
| (8) Water-dispersed composition of Example 1 | 0.5 |
| (9) Ethanol | 10.0 |

Preparation:
(1) through (9) are heated and uniformly dispersed. The dispersion was cooled to room temperature to obtain a hair mist.

The hair mist thus obtained was a hair mist excellent in the effect of protecting the hair from ultraviolet damages and not sticky.

EXAMPLE 18

Emulsion Eyeshadow

An eyeshadow of the composition below was prepared in the preparation below.

| Composition | (%) |
|---|---|
| (1) Talc | 10.0 |
| (2) Lauroyl lysine | 2.0 |
| (3) Coloring agent | 5.0 |
| (4) Titanated mica | 15.0 |
| (5) Stearic acid | 3.0 |
| (6) Octyldodecyl isostearate | 8.0 |
| (7) Squalene | 2.0 |
| (8) Octyl methoxycinnamate | 2.0 |
| (9) Propylene glycol monolaurate | 3.0 |
| (10) Purified water | Balance |
| (11) Water-dispersed composition of Example 1 | 5.0 |
| (12) 1,3-Butylene glycol | 6.0 |
| (13) Triethanolamine | 1.2 |
| (14) Preservative | q.s. |
| (15) Chelator | q.s. |

Preparation:
Powder components (5) through (9), stirred and mixed by a Henschel mixer in advance, are added to water phase components (1) through (4) to be uniformly dispersed by a mixer. (10) through (15) are heated and dissolved in another container. The dispersions of (1) through (4) and (5) through (9) were added to the mixture of (10) through (15) and emulsified, followed by cooling to room temperature to obtain an emulsion eyeshadow.

The emulsion eyeshadow thus obtained was excellent in ultraviolet prevention effect and product stability.

EXAMPLE 19

Aqueous Gel

An aqueous gel of the composition below was prepared in the preparation below:

| Composition | (%) |
|---|---|
| (1) Carboxyvinyl polymer | 0.2 |
| (2) Xanthan gum | 0.1 |
| (3) Purified water | Balance |
| (4) Triethanolamine | 0.1 |
| (5) POE (50) hydrogenated castor oil isostearate | 0.3 |
| (6) Fragrance | q.s. |
| (7) Ethanol | 10.0 |
| (8) Glycerol | 5.0 |
| (9) Dipropylene glycol | 5.0 |
| (10) Polyoxyethylene methyl glucoside | 5.0 |
| (11) Zinc oxide | 2.0 |
| (12) Titanium oxide | 2.0 |
| (13) Polyoxyethylene lauryl ether phosphate | 2.0 |
| (14) Water-dispersed composition of Example 1 | 8.0 |

Preparation
(1) through (4) are uniformly mixed and swelled. (5) through (7) are uniformly mixed in another container. (8) through (13) are uniformly dispersed by a homogenizer. The (5) through (7) and (8) through (13) and (14) were added to the (1) through (4) and uniformly dispersed to obtain an aqueous gel.

The aqueous gel thus obtained was an aqueous gel which, when applied on the skin, easily spreads and not sticky with refreshing feel.

Since the water-dispersed composition of the present invention can, even in the presence of salt, inhibit the agglomeration of benzotriazole-type ultraviolet absorbers and maintain the stably dispersed state, combination in cosmetics enables to exhibit the ultraviolet absorption action, and in addition, prevent color degradation due to light of contained dyes to maintain good color tone. This is accordingly extremely useful as a composition for cosmetics.

The invention claimed is:

1. An ultraviolet absorber water-dispersed composition, comprising the following components (A) and (B);
(A) a benzotriazole-type ultraviolet absorber represented by formula (1) below

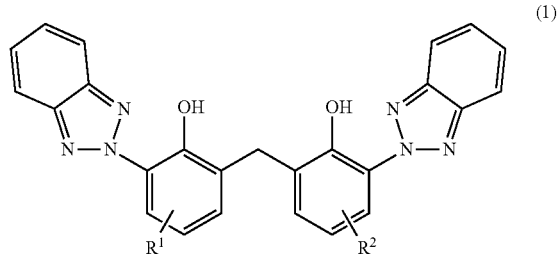

(1)

wherein $R^1$ and $R^2$ denote alkyl groups having a carbon number from 1 to 18, may be identical or different, and may be substituted by one or two or more groups selected from the group consisting of alkyl groups having a carbon number from 1 to 4, and cycloalkyl groups and aryl groups both having a carbon number from 5 to 12 and
(B) polyglycerol monoalkyl ester with a mean degree of polymerization or glycerol of 5 or more selected from the group consisting of decaglyceryl laurate and pentaglyceryl laurate.

2. The ultravioiet absorber water-dispersed composition of claim 1, wherein component (A) has a mean particle diameter of from 10 nm to 2000 nm.

3. The ultraviolet absorber water-dispersed composition of claim 1, wherein each of $R^1$ and $R^2$ in the general formula (1) of component (A) is a 1,1,3,3-tetramethyl butyl group.

4. The ultraviolet absorber water-dispersed composition of claim 1, wherein component (A) is contained from 10 mass % to 50 mass %.

5. The ultraviolet absorber water-dispersed composition of claim 1, wherein component (B) has an HLB of 14.5 or more.

6. The ultraviolet absorber water-dispersed composition of claim 5, wherein component (B) having the HLB of 14.5 or more is decaglyceryl caprate or decaglyceryl laurate.

7. The ultraviolet absorber water-dispersed composition of claim 1, wherein a mass ratio of a content of component (B):(A) is from 0.05:0.5.

8. A cosmetic comprising the ultraviolet absorber water-dispersed composition of claim 1.

9. The cosmetic of claim 8, further comprising octyl methoxycinnamate.

\* \* \* \* \*